United States Patent
Restle et al.

(12) 
(10) Patent No.: US 6,555,100 B1
(45) Date of Patent: Apr. 29, 2003

(54) COMPOSITIONS FOR TREATING KERATINOUS MATERIALS CONTAINING A COMBINATION OF A ZWITTERION POLYMER AND A WATER INSOLUBLE NON-VOLATILE SILICON

(75) Inventors: Serge Restle, Saint Prix (FR); Danièle Cauwet-Martin, Paris (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/380,087

(22) PCT Filed: Dec. 10, 1998

(86) PCT No.: PCT/FR98/02688

§ 371 (c)(1),
(2), (4) Date: Oct. 19, 1999

(87) PCT Pub. No.: WO99/34770

PCT Pub. Date: Jul. 15, 1999

(30) Foreign Application Priority Data

Dec. 31, 1997 (FR) .............................. 97 16807

(51) Int. Cl.$^7$ .............................. A61K 7/06; A61K 7/11
(52) U.S. Cl. ................ 424/70.1; 424/70.11; 424/70.12; 424/70.16
(58) Field of Search ................ 424/401, 70.1, 424/70.11, 70.12, 70.16; 510/119, 122, 123, 129

(56) References Cited

U.S. PATENT DOCUMENTS 2,528,378 A    10/1950   Mannheimer (List continued on next page.)

FOREIGN PATENT DOCUMENTS

| | | |
|---|---|---|
| DE | 39 29 973 | 3/1991 |
| DE | 40 04 953 | 10/1992 |
| EP | 0 014 479 | 8/1980 |
| EP | 0 047 714 | 3/1982 |
| EP | 0 185 507 | 6/1986 |
| EP | 0 217 274 | 4/1987 |
| EP | 0 412 704 | 2/1991 |
| EP | 0 412 707 | 2/1991 |
| EP | 0 492 657 | 7/1992 |
| EP | 0 535 447 | 4/1993 |
| EP | 0 577 636 | 1/1994 |
| EP | 0 582 152 | 2/1994 |
| EP | 0 604 717 | 7/1994 |
| EP | 0 605 503 | 7/1994 |
| EP | 0 761 206 | 3/1997 |
| FR | 2 641 185 | 7/1990 |
| FR | 2 470 596 | 6/1991 |
| GB | 2 104 091 | 3/1983 |
| JP | 59-24708 | 2/1984 |
| WO | WO 91/03229 | 3/1991 |
| WO | WO 92/17153 | 10/1992 |
| WO | WO 93/02196 | 2/1993 |
| WO | WO 93/05756 | 4/1993 |
| WO | WO 93/21897 | 11/1993 |
| WO | WO 93/23009 | 11/1993 |
| WO | WO 93/23446 | 11/1993 |
| WO | WO 94/01076 | 1/1994 |
| WO | WO 94/01078 | 1/1994 |
| WO | WO 94/07458 | 4/1994 |
| WO | WO 94/27570 | 12/1994 |
| WO | WO 95/00578 | 1/1995 |
| WO | WO 95/03776 | 2/1995 |
| WO | WO 95/05158 | 2/1995 |
| WO | WO 95/19757 | 7/1995 |
| WO | WO 97/35544 | 10/1997 |

OTHER PUBLICATIONS

English language Derwent Abstract of DE 39 29 973, Feb.–1991.

(List continued on next page.)

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

The invention relates to a composition for treating keratin substances, in particular the hair, containing, in a cosmetically and/or dermatologically acceptable aqueous medium, at least:

a) one zwitterionic polymer resulting from the copolymerization of at least one monomer of formula (I):

$$R_1-CH=C-C-Z-(C_nH_{2n})-\overset{R_3}{\underset{R_4}{\overset{|}{N^+}}}-R_5 \quad A^- \quad (I)$$
$$\underset{R_2}{|} \quad \underset{O}{\|}$$

in which $R_1$ and $R_2$, which may be identical or different, represent a hydrogen atom or a methyl radical, and $R_3$, $R_4$ and $R_5$, which may be identical or different, represent a linear or branched alkyl radical containing from 1 to 4 carbon atoms, Z represents an NH group or an oxygen atom,
n is an integer from 2 to 5,
$A^-$ is an anion derived from an organic or inorganic acid,
and at least one monomer of formula (II):

$$R_6-CH=CR_7-COOH \quad (II)$$

in which $R_6$ and $R_7$, which may be identical or different, represent a hydrogen atom or a methyl radical;
the said polymer being soluble in water to a concentration of 1% by weight at a pH below 6 and at 20° C.;

b) one non-amino, non-volatile, water-insoluble silicone with a viscosity of greater than $3 \times 10^{-5}$ m$^2$/s (300 centistokes).

66 Claims, No Drawings

U.S. PATENT DOCUMENTS

| | | |
|---|---|---|
| 2,781,354 A | 2/1957 | Mannheimer |
| 3,836,537 A | 9/1974 | Boerwinkle et al. |
| 4,075,131 A | 2/1978 | Sterling |
| 4,415,417 A | 11/1983 | Bush et al. |
| 4,693,935 A | 9/1987 | Mazurek |
| 4,728,571 A | 3/1988 | Clemens et al. |
| 4,784,789 A | 11/1988 | Jeschke et al. |
| 4,972,037 A | 11/1990 | Garbe et al. |
| 5,631,003 A | 5/1997 | Mueller et al. |
| 5,650,383 A * | 7/1997 | Dubief et al. |
| 5,756,076 A | 5/1998 | Cervantes et al. |
| 5,985,295 A * | 11/1999 | Peffly |

OTHER PUBLICATIONS

English language Derwent Abstract of DE 40 04 953, May–1991.

English language Derwent Abstract of EP 0 014 479, Aug. 1980.

English language Derwent Abstract of EP 0 047 714, Feb.–1982.

English language Derwent Abstract of EP 0 535 447, Apr.–1993.

English language Derwent Abstract of EP 0 577 636, Feb.–1994.

English language Derwent Abstract of EP 0 604 717, Jul. 1994.

English language Derwent Abstract of EP 0 605 503, Jul. 1994.

English language Derwent Abstract of EP 0 761 206, Mar. 1997.

English language Derwent Abstract of FR 2 470 596, Dec. 1981.

English language Derwent Abstract of FR 2 641 185, Jun.–1990.

English language Derwent Abstract of JP 59–024708, Feb.–1984.

* cited by examiner

COMPOSITIONS FOR TREATING KERATINOUS MATERIALS CONTAINING A COMBINATION OF A ZWITTERION POLYMER AND A WATER INSOLUBLE NON-VOLATILE SILICON

This application is a PCT/FR98/02688, filed Dec. 10, 1998.

The present invention relates to novel compositions for treating keratin substances, in particular the hair, containing a combination of a zwitterionic polymer and a non-amino, non-volatile, water-insoluble silicone, and to their uses and processes.

Hair conditioners which provide additional cosmetic effects after application and rinsing, such as softness, flexibility, good disentangling, a sheen effect and/or a styling effect, have been sought in recent years in the field of shampoos and conditioners.

It is known in the prior art that silicones are cosmetic products which are particularly desired in hair formulations for their hair-conditioning properties, their softening and disentangling properties and for the sheen effect they provide. When they are used in rinse-out hair compositions, these ingredients have the drawback of being difficult to deposit on the hair and to do so in a non-uniform manner when applied and after rinsing, and of not being able to give the hair the desired effects intrinsic to silicones.

Shampoo compositions based on zwitterionic polymers comprising a monomer of quaternary ammonium type and a monomer of carboxylic acid type are envisaged in patent application WO 91/03229. These polymers, used alone, do not make it possible to obtain satisfactory cosmetic properties either.

Combining silicones with an amphoteric polymer of the acrylic acid/diallyldimethylammoniun chloride type has also been envisaged in patent U.S. Pat. No. 5,650,383. These combinations are still not entirely satisfactory.

The Applicant has now discovered that by combining specific zwitterionic polymers with non-amino, non-volatile, water-insoluble silicones of viscosity which will be defined later, it is possible to obtain, surprisingly, cosmetic compositions based on non-amino silicones which do not have the drawbacks mentioned above, and which give enhanced cosmetic performance, in particular as regards the feel and the disentangling, as well as good styling properties.

In particular, this combination promotes the deposition of silicone onto keratin substances.

Moreover, the Applicant has discovered, unexpectedly, that by combining the silicones of the invention with the zwitterionic polymers defined below, the cosmetic performance of the zwitterionic polymer is markedly enhanced.

A subject of the invention is thus cosmetic or dermatological compositions, characterized in that they comprise, in a cosmetically and/or dermatologically acceptable aqueous medium, at least:

a) one zwitterionic polymer resulting from the copolymerization of at least one monomer of formula (I):

$$R_1-CH=\underset{R_2}{\underset{|}{C}}-\underset{O}{\underset{\|}{C}}-Z-(C_nH_{2n})-\underset{R_4}{\underset{|}{N^+}}-R_5 \quad A^- \quad (I)$$

in which $R_1$ and $R_2$, which may be identical or different, represent a hydrogen atom or a methyl radical, and $R_3$, $R_4$ and $R_5$, which may be identical or different, represent a linear or branched alkyl radical containing from 1 to 4 carbon atoms, Z represents an NH group or an oxygen atom, n is an integer from 2 to 5, $A^-$ is an anion derived from an organic or inorganic acid, and at least one monomer of formula (II):

$$R_6-CH=CR_7-COOH \quad (II)$$

in which $R_6$ and $R_7$, which may be identical or different, represent a hydrogen atom or a methyl radical;

the said polymer being soluble in water to a concentration of 1% by weight at a pH below 6 and at 20° C.;

b) one non-amino, non-volatile, water-insoluble silicone with a viscosity of greater than $3 \times 10^{-5}$ m$^2$/s (300 centistokes).

A subject of the invention is also the use of a zwitterionic polymer defined above in a composition comprising a non-amino, non-volatile, water-insoluble silicone to enhance the conditioning effect of the silicone.

According to the present invention, the expression "keratin substances" means the hair, the eyelashes, the eyebrows, the skin, the nails, mucous membranes or the scalp, and more particularly the hair.

The monomers of formula (I) of the present invention are preferably chosen from the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, which are quaternized, for example, with a $C_1-C_4$ alkyl halide or a $C_1-C_4$ dialkyl sulphate.

More particularly, the monomer of formula (I) is chosen from acrylamidopropyltrimethylammonium chloride and methacrylamidopropyltrimethylammonium chloride.

The monomers of formula (II) of the present invention are preferably chosen from the group consisting of acrylic acid, methacrylic acid, crotonic acid and 2-methylcrotonic acid.

More particularly, the monomer of formula (II) is acrylic acid.

The monomers constituting the zwitterionic polymers of the invention are preferably preneutralized and/or prequaternized.

The ratio of the number of cationic charges/anionic charges is generally less than 1.

The weight-average molecular weights of the zwitterionic polymers can range from 500 to 50,000,000 and are preferably between 10,000 and 5,000,000.

The polymers according to the invention can also contain other monomers, such as nonionic monomers and in particular such as $C_1-C_4$ alkyl acrylates or methacrylates.

The zwitterionic polymers according to the invention are described, for example, in patent application DE 3,929,973.

The zwitterionic polymers which are particularly preferred according to the invention are chosen from acrylic acid/acrylamidopropyl-trimethylammonium chloride copolymers and acrylic acid/methacrylamidopropyltrimethylammonium chloride copolymers.

Acrylic acid/acrylamidopropyltrimethyl-ammonium chloride/methyl acrylate terpolymers can also be used, for example those sold under the name Merquat 2001 by the company Calgon.

The silicones of the invention preferably have a viscosity of greater than $5 \times 10^{-5}$ m$^2$/s (500 centistokes) and more particularly greater than $10 \times 10^{-5}$ m$^2$/s (1000 centistokes). Preferably, the silicones have a viscosity of less than 50,000,000 mm$^2$/s. The viscosities are measured at 25° C.

In all the text hereinabove and hereinbelow, in accordance with that which is generally accepted, the terms "silicone" and "polysiloxane" are intended to denote any organosilicon polymer or oligomer of linear or cyclic, branched or crosslinked structure, of variable molecular weight, obtained by polymerization and/or polycondensation of suitably functionalized silanes, and consisting essentially of a repetition of main units in which the silicon atoms are linked together by oxygen atoms (siloxane bond ≡Si—O—Si≡), optionally substituted hydrocarbon-based radicals being linked directly via a carbon atom to the said silicon atoms. The hydrocarbon-based radicals most commonly used are alkyl radicals, in particular $C_1$–$C_{10}$ alkyls and in particular methyl, fluoroalkyl radicals, aryl radicals and in particular phenyl, and alkenyl radicals and in particular vinyl; other types of radicals which can be linked, either directly or via a hydrocarbon-based radical, to the siloxane chain are, in particular, hydrogen, halogens and in particular chlorine, bromine or fluorine, thiols, alkoxy radicals, polyoxyalkylene radicals (or polyethers) and in particular polyoxyethylene and/or polyoxypropylene, hydroxyl or hydroxyalkyl radicals, amide groups, acyloxy or acyloxyalkyl radicals, anionic groups such as carboxylates, thioglycolates, sulphosuccinates, thiosulphates, phosphates and sulphates, needless to say this list not being in any way limiting (so-called "organomodified" silicones).

According to the invention, the term "non-amino silicone" denotes any silicone not comprising at least one primary amine or a quaternary ammonium group.

Among the silicones of the invention with a viscosity of greater than $3 \times 10^{-3}$ m$^2$/s, mention may be made of:

(i) polyalkylsiloxanes;
(ii) polyarylsiloxanes;
(iii) polyalkylarylsiloxanes;
(iv) silicone gums;
(v) silicone resins;
(vi) polyorganosiloxanes containing in their general structure one or more organofunctional groups directly attached to the siloxane chain or attached via a hydrocarbon-based radical;
(vii) block copolymers having a polysiloxane-polyoxyalkylene linear block as repeating units;
(viii) grafted silicone polymers containing a non-silicone organic skeleton, consisting of an organic main chain formed from organic monomers not containing silicone, onto which is grafted, within the said chain as well as, optionally, on at least one of its ends, at least one polysiloxane macromonomer;
(ix) grafted silicone polymers containing a polysiloxane skeleton, grafted with non-silicone organic monomers, comprising a polysiloxane main chain onto which is grafted, within the said chain as well as, optionally, on at least one of its ends, at least one organic macromonomer not containing silicone;
(x) or mixtures thereof.

Among the polyalkylsiloxanes, mention may be made mainly of:

linear polydimethylsiloxanes containing trimethylsilyl end groups, such as, for example, and in a non-limiting manner, the Silbione oils of the 70047 series sold by Rhône-Poulenc; the oil 47 V 500 000 from Rhône-Poulenc or certain Viscasil oils from General Electric;

linear polydimethylsiloxanes containing hydroxydimethylsilyl end groups, such as the oils of the 48 V series from Rhône-Poulenc.

In this class of polyalkylsiloxanes, mention may also be made of the polyalkylsiloxanes sold by the company Goldschmidt under the trade names Abilwax 9800 and Abilwax 9801, which are poly($C_1$–$C_{20}$)alkylsiloxanes.

Among the polyalkylarylsiloxanes, mention may be made of linear or branched polydimethylmethylphenyl-siloxanes and polydimethyldiphenylsiloxanes, such as the product DC 556 Cosmetic Grade Fluid from Dow Corning.

The silicone gums in accordance with the invention are polyorganosiloxanes with an average molecular mass of between 200,000 and 1,000,000, used alone or as a mixture in a solvent chosen from the group consisting of volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention is made, for example, of the following compounds:

poly dimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)].

Mention may be made, for example, of the following mixtures:

1) mixtures formed from a polydimethyl-siloxane hydroxylated at the end of the chain (Dimethiconol according to the CTFA nomenclature) and from a cyclic polydimethylsiloxane (Cyclomethicone), such as the product Q2 1401 sold by the company Dow Corning;

2) mixtures formed from a polydimethylsiloxane gum with a cyclic silicone, such as the product SF 1214 Silicone Fluid from General Electric, which is an SE 30 gum of molecular weight 500,000 dissolved in SF 1202 Silicone Fluid (decamethylcyclopentasiloxane);

3) mixtures of two polydimethylsiloxanes (PDMS) of different viscosity, in particular a PDMS gum and a PDMS oil, such as the products SF 1236 and CF 1241 from General Electric. The product SF 1236 is a mixture of an SE 30 oil defined above, with a viscosity of 20 m$^2$/s, and of an SF 96 oil with a viscosity of $5 \times 10^{-5}$ m$^2$/s (15% SE 30 gum and 85% SF 96 oil). The product CF 1241 is a mixture of an SE 30 gum (33%) and of a PDMS (67%) with a viscosity of $10^{-3}$ m$^2$/s.

The silicone resins in accordance with the invention are preferably crosslinked siloxane systems containing the units:

$R_2SiO_{2/2}$, $RSiO_{3/2}$ and $SiO_{4/2}$, in which R denotes a hydrocarbon-based group having 1 to 6 carbon atoms or a phenyl group. Among these products, the ones which are particularly preferred are those in which R denotes a lower alkyl radical or a phenyl radical.

Among these resins, mention may be made of the product sold under the name Dow Corning 593 by Dow Corning or those sold under the name Silicone Fluid SS 4267 by General Electric and which are dimethyl/trimethylpolysiloxanes.

The organomodified polyorganosiloxanes of the invention are polyorganosiloxanes as defined above, containing in their general structure one or more organofunctional groups directly attached to the siloxane chain or attached via a hydrocarbon-based radical.

Mention is made, for example, of polyorganosiloxanes containing:

a) polyethylenoxy and/or polypropylenoxy groups, optionally containing alkyl groups, such as the product known as lauryl methicone copolyol sold under the name Q2 5200 by Dow Corning;

b) (per)fluoro groups, for instance trifluoroalkyl groups such as, for example, those sold by Shin Etsu under the name FL 100;

c) thiol groups;

d) carboxylate groups, such as the products described in European patent EP 185 507 from Chisso Corporation;

e) hydroxylated groups, such as the polyorganopolysiloxanes containing a hydroxyalkyl function, described in French patent application FR 85/16334, and in particular polyorganopolysiloxanes containing a γ-hydroxypropyl function;

f) alkoxylated groups containing at least 12 carbon atoms, such as the product Silicone Copolymer F755 from SWS Silicones and the products Abilwax 2428, Abilwax 2434 and Abilwax 2440 from the company Goldschmidt;

g) acyloxyalkyl groups containing at least 12 carbon atoms, such as the polyorganosiloxanes described in French patent application FR 88/17433 and in particular polyorganosiloxanes containing a stearoyloxypropyl function;

h) amphoteric groups;

i) bisulphite groups.

The block copolymers having a polysiloxane-polyoxyalkylene linear block as repeating unit, which are used in the context of the present invention, preferably have the following general formula:

$$([Y(R_2SiO)_a R'_2SiYO][(CnH_{2n}O)_b])_c \quad (V)$$

in which:

R and R', which may be identical or different, represent a monovalent hydrocarbon-based radical containing no aliphatic unsaturation, n is an integer ranging from 2 to 4, a is an integer greater than or equal to 5, preferably between 5 and 200 and even more particularly between 5 and 100, b is an integer greater than or equal to 4, preferably between 4 and 200 and even more particularly between 5 and 100, c is an integer greater than or equal to 4, preferably between 4 and 1000 and even more particularly between 5 and 300, Y represents a divalent organic group which is linked to the adjacent silicon atom via a carbon-silicon bond and to a polyoxyalkylene block via an oxygen atom, the average molecular weight of each siloxane block is between about 400 and about 10,000, that of each polyoxyalkylene block being between about 300 and about 10,000, the siloxane blocks represent from about 10% to about 95% of the weight of the block copolymer, the average molecular weight of the block copolymer being at least 3000 and preferably between 5000 and 1,000,000 and even more particularly between 10,000 and 200,000.

R and R' are preferably chosen from the group comprising alkyl radicals such as, for example, the methyl, ethyl, propyl, butyl, pentyl, hexyl, octyl, decyl and dodecyl radicals, aryl radicals such as, for example, phenyl and naphthyl, aralkyl radicals such as, for example, benzyl and phenylethyl, and tolyl, xylyl and cyclohexyl radicals.

Y is preferably —R"—, —R"—CO—, —R"—NHCO—, —R"—NH—CO—NH—R"'—NHCO or —R"—OCONH—R"'—NHCO—, where R" is a divalent alkylene group such as, for example, ethylene, propylene or butylene, and R"' is a divalent alkylene group or a divalent arylene group such as —C$_6$H$_4$—, —C$_6$H$_4$—C$_6$H$_4$—, —C$_6$H$_4$—CH$_2$—C$_6$H$_4$—or — C$_6$H$_4$—C(CH$_3$)$_2$—C$_6$H$_4$—.

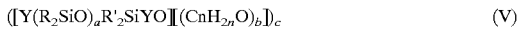

Even more preferably, Y represents a divalent alkylene radical, more particularly the —CH$_2$—CH$_2$—CH$_2$— radical or the C$_4$H$_8$ radical.

The preparation of the block copolymers used in the context of the present invention is described in European application EP 0,492,657 A1, the teaching of which is included by way of reference in the present description.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578, the teachings of which are included in their entirety in the present description by way of non-limiting references. They are copolymers obtained by radical polymerization from monomers containing ethylenic unsaturation and from silicone macromers having a vinyl end group, or alternatively copolymers obtained by reaction of a polyolefin comprising functionalized groups and of a polysiloxane macromer having an end function which is reactive with the said functionalized groups.

Examples of polymers containing a polysiloxane skeleton grafted with non-silicone organic monomers, which are suitable for carrying out the present invention, as well as the particular method for preparing them, are described in particular in patent applications EP-A-0,582,152, WO 93/23009 and WO 95/03776, the teachings of which are included in their entirety in the present description by way of non-limiting references.

The zwitterionic polymers of the invention are present in the compositions of the invention in proportions preferably ranging from 0.01 to 20% by weight and more particularly from 0.1 to 10% by weight relative to the total weight of the composition.

The silicones of the invention are generally present in the compositions in proportions ranging from 0.001 to 20% by weight and preferably from 0.01 to 10% by weight relative to the total weight of the composition.

The pH of the aqueous compositions in accordance with the invention is preferably adjusted to between 3 and 11 and more particularly to between 5 and 9, by using buffers or basifying or acidifying agents.

Particularly when they are in the form of a shampoo, the compositions according to the invention comprise a washing base, which is generally aqueous.

The surfactant(s) forming the washing base can be chosen, equally, alone or as mixtures, from anionic, amphoteric, nonionic, zwitterionic and cationic surfactants.

The minimum amount of washing base is that which is just sufficient to give the final composition a satisfactory foaming and/or detergent power.

Thus, according to the invention, the washing base can represent from 4% to 30% by weight, preferably from 10% to 25% by weight and even more preferably from 12% to 20% by weight, relative to the total weight of the final composition.

The surfactants which are suitable for carrying out the present invention are, in particular, the following:

(i) Anionic Surfactant(s):

In the context of the present invention, their nature is not really a critical feature.

Thus, by way of example of anionic surfactants which can be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulphates, alkyl ether sulphates, alkylamido ether sulphates, alkylaryl polyether sulphates, monoglyceride sulphates; alkyl sulphonates, alkyl phosphates, alkylamide sulphonates, alkylaryl sulphonates, (x-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyl taurates, the alkyl or acyl radical of all of these different compounds preferably containing from 8 to 24 carbon atoms and the aryl radical preferably denoting a phenyl or benzyl group. Among the anionic surfactants which can also be used, mention may also be made of fatty acid salts such as oleic, ricinoleic, palmitic and stearic acid salts, copra oil acid or hydrogenated copra oil acid; acyl lactylates in which the acyl radical contains 8 to 20 carbon atoms. It is also possible to use weakly anionic surfactants, such as alkyl D-galactosiduronic acids and their salts, as well as polyoxyalkylenated carboxylic ether ($C_6$–$C_{24}$)alkyl acids, polyoxyalkylenated carboxylic ether ($C_6$–$C_{24}$)alkylaryl acids, polyoxyalkylenated carboxylic ether ($C_6$–$C_{24}$)alkylamido acids and their salts, in particular those containing from 2 to 50 ethylene oxide groups, and mixtures thereof.

Among the anionic surfactants, the ones preferably used according to the invention are alkyl sulphate salts and alkyl ether sulphate salts and mixtures thereof.

(ii) Nonionic Surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-solubilizing anionic group (for example carboxylate, sulphonate, sulphate, phosphate or phosphonate); mention may also be made of ($C_8$–$C_{20}$)alkylbetaines, sulphobetaines, ($C_8$–$C_{20}$)alkylamido($C_1$–$C_6$) alkylbetaines or ($C_8$–$C_{20}$) alkylamido($C_1$–$C_6$) alkylsulphobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

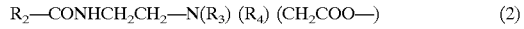

$$R_2\text{—CONHCH}_2\text{CH}_2\text{—N}(R_3)\,(R_4)\,(\text{CH}_2\text{COO—}) \qquad (2)$$

in which: $R_2$ denotes an alkyl radical of an acid $R_2$—COOH present in hydrolysed copra oil, a heptyl, nonyl or undecyl radical, $R_3$ denotes a β-hydroxyethyl group and $R_4$ denotes a carboxymethyl group; and

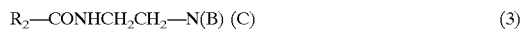

$$R_2\text{—CONHCH}_2\text{CH}_2\text{—N(B) (C)} \qquad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_2$, denotes an alkyl radical of an acid $R_9$—COOH present in copra oil or in hydrolysed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

By way of example, mention may be made of the cocoamphocarboxyglycinate sold under the trade name Miranol $C_2M$ concentrate by the company Miranol.

(iv) Cationic Surfactants:

Among the cationic surfactants, whose nature, in the context of the present invention, is not a critical feature, mention may be made in particular (non-limiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The cosmetically or dermatologically acceptable medium of the compositions of the invention is preferably water or an aqueous-alcoholic solution of a lower alcohol such as ethanol, isopropanol or butanol.

The composition of the invention can also contain at least one additive chosen from sequestering agents, softeners, foam modifiers, dyes, pearlescent agents, moisturizers, anti-dandruff agents, anti-seborrhoeic agents, suspending agents, ceramides, pseudoceramides, fatty acids containing linear or branched $C_{16}$–$C_{40}$ chains, hydroxy acids, electrolytes, thickeners, fatty acid esters, fatty acid esters of glycerol, surfactants, fragrances, preserving agents, silicone or non-silicone sunscreens, proteins, vitamins, ionic or nonionic polymers, water-soluble silicones, plant, animal, mineral or synthetic oils and any other additive conventionally used in the cosmetics field.

These additives are present in the composition according to the invention in proportions which can range from 0 to 40% by weight relative to the total weight of the composition. The precise amount of each additive depends on its nature and is readily determined by a person skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

These compositions can be in the form of relatively thickened liquids, creams or gels and they are mainly suitable for washing, conditioning and/or styling the hair. They can also be in the form of rinse-out lotions.

Another subject of the invention consists of a cosmetic treatment process for the hair, characterized in that a composition as defined above is applied directly to the said wet substances and, after optionally leaving it thereon for a period of time, it is rinsed out with water; the said process can be repeated several times.

As mentioned above, the compositions according to the invention give the hair, after rinsing, a noteworthy conditioning effect which is manifested in particular by an ease of disentangling the hair, as well as properties of softness and smoothness of the hair, lightness and volume.

The examples which follow serve to illustrate the present invention without, however, being limiting in nature.

EXAMPLE 1

Two shampoo compositions, one in accordance with the invention (composition A) and the other comparative (composition B), were prepared:

| | A Invention | B Comparative |
|---|---|---|
| Sodium lauryl ether sulphate (70/30 $C_{12}/C_{14}$) containing 2.2 mol of ethylene oxide | 3 g AM | 3 g AM |
| Sodium laurylamido ether (3 EO) carboxylate containing 30% AM (Akypo Foam 30 BV from KAO) | 12 g AM | 12 g AM |
| Silicone (60,000 cST) (*) | 2 g | 2 g |
| Copolymer of diallyldimethyl-ammonium chloride and acrylic acid (Merquat 280 from Calgon) | — | 2 g AM |
| Acrylic acid/methacrylamido-propyltrimethylammonium chloride co-polymer as aqueous solution containing 10% AM | 2 g AM | — |
| 1-(Hexadecyloxy)-2-octadecanol/cetyl alcohol mixture | 2.5 g | 2.5 g |
| Copra acid monoisopropanoiamide | 1.5 g | 1.5 g |
| NaOH qs pH | | 7.5 |
| HCl qs pH | 7.5 | |
| Demineralized water qs | 100 g | 100 g |

(*): Polydimethylsiloxane of viscosity 60,000 cSt sold by the company Dow Corning under the name Fluid DC 200–60,000 cSt.

Shampooing is carried out by applying about 1 g of composition A to locks of 2.5 g of premoistened natural hair. The shampoo is worked into a lather, left to stand on the hair for 10 minutes and then rinsed out thoroughly with water. The locks are dried at 60° C. for 30 minutes. The same procedure as above is carried out with the comparative composition B.

Analytically, it was shown that the deposition of silicone on the hair is better with composition A according to the invention.

EXAMPLE 2

A shampoo of the composition below is prepared:

| | |
|---|---|
| $C_9/C_{11}$ alkyl polyglucoside (1.4) as an aqueous 40% solution, sold by KAO under the name KAG 40 | 10 g AM |
| Sodium laurylamido ether (3 EO) carboxylate containing 30% AM in water, sold by KAO under the name Akypo Foam 30 BV | 5 g AM |
| Acrylic acid/methacryloamidopropyltrimethyl-ammonium chloride/methyl acrylate terpolymer as an aqueous 20% solution, sold under the name Merquat 2001 by Calgon | 1 g AM |
| Polydimethylsiloxane (viscosity 250,000 cSt), sold under the name Mirasil DM 500,000 by the company Rhône-Poulenc | 1 g |
| Copra acid monoisopropanolamide | 2 g |
| 1-(Hexadecyloxy)2-octadecanol/cetyl alcohol mixture | 2.5 g |
| Crosslinked polyacrylic acid sold under the name Carbopol 980 by Goodrich | 0.5 g |
| Preserving agents, fragrance | qs |
| Water | qs 100 g |
| pH adjusted to 6 (NaOH) | |

A shampoo with good lathering properties, a good styling effect and which gives dry hair a smooth, soft feel is obtained.

EXAMPLE 3

A shampoo of the composition below is prepared:

| | |
|---|---|
| Ammonium lauryl sulphate as an aqueous solution containing 30% AM (Empicol AL 30/FL from Albright and Wilson) | 12 g AM |
| Poly(methylpolyoxyethylenated dimethyl methylcetyl)siloxane of viscosity 5000 cSt (Abil EM 90 from Goldschmidt) | 2 g |
| Ethyl glycol distearate | 1 g AM |
| Copra diethanolamide | 2 g AM |
| Acrylamidopropyltrimethylammoniun chloride/sodium acrylate copolymer as an aqueous solution containing 37% AM (Polyquart KE 3033 from Henkel) | 1.5 g AM |
| Preserving agents, fragrance | qs |
| Water | qs 100 g |
| pH adjusted to 7 (HCl) | |

A shampoo which has good lathering properties, a good styling effect and which gives dry hair a smooth, soft feel is obtained.

What is claimed is:

1. A cosmetic or dermatological rinse-out composition, comprising, in a cosmetically or dermatologically acceptable aqueous medium, a) at least one zwitterionic polymer resulting from the copolymerization of at least one monomer of formula (I):

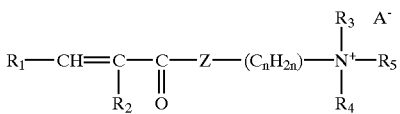

in which $R_1$ and $R_2$, which are identical or different, are chosen from a hydrogen atom and a methyl radical, and $R_3$, $R_4$ and $R_5$, which are identical or different, are chosen from linear and branched alkyl radicals containing from 1 to 4 carbon atoms, Z is chosen from an NH group and an oxygen atom, n is an integer from 2 to 5, $A^-$ is an anion of an organic or inorganic acid, and at least one monomer of formula (II):

in which $R_6$ and $R_7$, which are identical or different, are chosen from a hydrogen atom and a methyl radical;

wherein said at least one zwitterionic polymer is soluble in water to a concentration of 1% by weight at a pH below 6 and at 20° C.;

b) at least one non-amino, non-volatile, water-insoluble silicone having a viscosity of greater than 300 centistokes; and c) a washing base present in an amount ranging from 4 to 30% by weight relative to the total weight of the composition, wherein the washing base comprises at least one surfactant.

2. The composition according to claim 1, wherein said at least one non-amino, non-volatile, water-insoluble silicone has a viscosity of greater than 500 centistokes.

3. The composition according to claim 2, wherein said at least one non-amino, non-volatile, water-insoluble silicone has a viscosity of greater than 1000 centistokes.

4. The composition according to claim 1, wherein said at least one non-amino, non-volatile, water-insoluble silicone is chosen from:

(i) polyalkylsiloxanes;
(ii) polyarylsiloxanes;
(iii) polyalkylarylsiloxanes;
(iv) silicone gums;
(v) silicone resins;
(vi) polyorganosiloxanes containing one or more organofunctional groups directly attached to the siloxane chain or attached by way of a hydrocarbon-based radical;
(vii) block copolymers containing a polysiloxane-polyoxyalkylene linear block as a repeating unit;
(viii) grafted silicone polymers containing a non-silicone organic skeleton, comprising:
an organic main chain formed from organic monomers not containing silicone, and
at least one polysiloxane macromonomer which is grafted onto said organic main chain;
(ix) grafted silicone polymers containing a polysiloxane skeleton, comprising:
a polysiloxane main chain,
at least one organic macromonomer not containing silicon which is grafted onto said polysiloxane main chain;
(x) and mixtures thereof.

5. The composition according to claim 4, wherein for said grafted silicone polymers containing a non-silicone organic skeleton, at least one polysiloxane macromonomer is grafted to at least one end of said organic main chain, in addition to said at least one polysiloxane macromonomer grafted onto said organic main chain.

6. The composition according to claim 4, wherein for said grafted silicone polymers containing a polysiloxane skeleton, at least one organic macromonomer not containing silicon is grafted to at least one end of said polysiloxane main chain, in addition to said at least one organic macromonomer grafted onto said polysiloxane main chain.

7. The composition according to claim 4, wherein said polyalkylsiloxanes are chosen from:
linear polydimethylsiloxanes containing trimethylsilyl end groups, and
linear polydimethylsiloxanes containing hydroxydimethylsilyl end groups.

8. The composition according to claim 4, wherein said silicone gums are polydiorganopolysiloxanes having a number-average molecular mass ranging from 200,000 to 1,000,000.

9. The composition according to claim 4, wherein said silicone gums are chosen from:
polydimethylsiloxane,
poly((dimethylsiloxane)/(methylvinylsiloxane)),
poly((dimethylsiloxane)/(diphenylsiloxane)),
poly((dimethylsiloxane)/(phenylmethylsiloxane)),
poly((dimethylsiloxane)/(diphenylsiloxane)/(methylvinylsiloxane)).

10. The composition according to claim 4, wherein said silicone gums are chosen from:
a) mixtures formed from a polydimethylsiloxane hydroxylated at the end of the chain and a cyclic polydimethylsiloxane;
b) mixtures formed from a polydimethylsiloxane gum with a cyclic silicone; and
c) mixtures of a polydimethylsiloxane gum and a polydimethylsiloxane oil.

11. The composition according to claim 4, wherein said silicone resins are siloxane systems containing the units:
$R_2SiO_{2/2}$, $RSiO_{3/2}$, $SiO_{4/2}$, in which R is a hydrocarbon-based group containing from 1 to 6 carbon atoms or a phenyl group.

12. The composition according to claim 4, wherein said organomodified polyorganosiloxanes are chosen from those comprising:
a) polyethylenoxy groups, polypropylenoxy groups, and mixtures thereof;
b) (per)fluoro groups;
c) thiol groups;
d) carboxylate groups;
e) hydroxylated groups;
f) alkoxylated groups;
g) acyloxyalkyl groups;
h) amohoteric groups, and
i) bisulphite groups.

13. The composition according to claim 12, wherein said polyethylenoxy groups and polypropylenoxy groups further comprise alkyl groups.

14. The composition according to claim 4, wherein said block copolymers have the following formula:

in which:
R and R', which are identical or different, are monovalent hydrocarbon-based radicals containing no aliphatic unsaturation,
n is an integer ranging from 2 to 4,
a is an integer greater than or equal to 5,
b is an integer greater than or equal to 4,
c is an integer greater than or equal to 4,
Y is a divalent organic group which is linked to the adjacent silicon atom via a carbon-silicon bond and to a polyoxyalkylene block via an oxygen atom,
each siloxane block, which comprises $(Y(R_2SiO)_aR'_2SiYO)$, has an average molecular weight ranging from 400 to 10,000, and each polyoxyalkylene block, which comprises $((C_nH_{2n}O)_b)$, has an average molecular weight ranging from 300 to 10,000,
said siloxane blocks are present in an amount ranging from 10% to 95% of the total weight of said block copolymer, and
said block copolymer has an average molecular weight of at least 3000.

15. The composition according to claim 1, wherein said at least one non-amino, non-volatile, water-insoluble silicone is present in an amount ranging from 0.001 to 20% by weight relative to the total weight of the composition.

16. The composition according to claim 15, wherein said at least one non-amino, non-volatile, water-insoluble silicone is present in an amount ranging from 0.01 to 10% by weight relative to the total weight of the composition.

17. The composition according to claim 1, wherein said at least one monomer of formula (I) is chosen from the following monomers: dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide, wherein each of said monomers is quaternized.

18. The composition according to claim 17, wherein said monomers are quaternized with a $C_1$–$C_4$ alkyl halide or a $C_1$–$C_4$ dialkyl sulphate.

19. The composition according to claim 17, wherein said at least one monomer of formula (I) is chosen from acrylamidopropyltrimethylammonium chloride and methacrylamidopropyltrimethylarmmonium chloride.

20. The composition according to claim 1, wherein said at least one monomer of formula (II) is chosen from: acrylic acid, methacrylic acid, crotonic acid and 2-methyl-crotonic acid.

21. The composition according to claim 20, wherein said at least one monomer of formula (II) is acrylic acid.

22. The composition according to claim 1, wherein said at least one zwitterionic polymer is chosen from copolymers of acrylic acid and acrylamidopropyltrimethylammonium chloride, and copoylmers of acrylic acid and methacrylamidopropyltrimethylammonium chloride.

23. The composition according to claim 1, wherein said at least one zwitterionic polymer is present in a concentration ranging from 0.01 to 20% by weight relative to the total weight of the composition.

24. The composition according to claim 23, wherein said at least one zwitterionic polymer is present in a concentration ranging from 0.1 to 10% by weight relative to the total weight of the composition.

25. The composition according to claim 1, wherein said composition has a pH ranging from 3 to 11.

26. The composition according to claim 1, wherein the at least one surfactant is chosen from anionic, cationic, nonionic, amphoteric, and zwitterionic surfactants.

27. The composition according to claim 1, wherein said cosmetically or dermatologically acceptable aqueous medium comprises water or a mixture of water and at least one lower alcohol.

28. The composition according to claim 1, further comprising at least one additive chosen from sequestering agents, softeners, foam modifiers, dyes, pearlescent agents, moisturizers, antidandruff agents, anti-seborrhoeic agents, suspending agents, ceramides, pseudoceramides, fatty acids containing linear $C_{16}$–$C_{40}$ chains, fatty acids containing branched $C_{16}$–$C_{40}$ chains, hydroxy acids, electrolytes, thickeners, fatty acid esters, fatty acid esters of glycerol, surfactants, fragrances, preserving agents, silicone sunscreens, non-silicone sunscreens, proteins, vitamins, ionic or nonionic polymers, water-soluble silicones, plant oils, animal oils, mineral oils, and synthetic oils.

29. The composition according to claim 1, wherein said composition is a rinse-out product for washing, conditioning, or styling hair, or for a combination of any two or three of washing, conditioning, and styling hair.

30. A cosmetic or dermatological composition, comprising, in a cosmetically or dermatologically acceptable aqueous medium,
   a) acrylic acid/methacrylamidopropyltrimethylammonium chloride copolymer; and
   b) polydimethylsiloxane having a viscosity of 60,000 centistokes.

31. A cosmetic or dermatological composition, comprising, in a cosmetically or dermatologically acceptable aqueous medium,
   a) acrylic acid/methacryloamidopropyltrimethylammonium chloride/methyl acrylate terpolymer; and
   b) polydimethylsiloxane having a viscosity of 250,000 centistokes.

32. A cosmetic or dermatological composition, comprising, in a cosmetically or dermatologically acceptable aqueous medium,
   a) acrylamidopropyltrimethylammonium chloride/sodium acrylate copolymer; and
   b) poly(methylpolyoxyethylenated dimethyl methylcetyl) siloxane having a viscosity of 5000 centistokes.

33. A process for the cosmetic treatment of a keratin substance, comprising:
   applying to a wet keratin substance a cosmetic or dermatological composition, comprising, in a cosmetically or dermatologically acceptable aqueous medium,
      a) at least one zwitterionic polymer resulting from the copolymerization of at least one monomer of formula (I):

$$R_1-CH=C(R_2)-\underset{O}{\overset{\parallel}{C}}-Z-(C_nH_{2n})-\overset{R_3}{\underset{R_4}{N^+}}-R_5 \quad A^- \tag{I}$$

in which $R_1$ and $R_2$, which are identical or different, are chosen from a hydrogen atom and a methyl radical, and $R_3$, $R_4$ and $R_5$, which are identical or different, are chosen from linear and branched alkyl radicals containing from 1 to 4 carbon atoms, Z is chosen from an NH group and an oxygen atom,
n is an integer from 2 to 5,
A⁻ is an anion of an organic or inorganic acid,
with at least one monomer of formula (II):

in which $R_6$ and $R_7$, which are identical or different, are chosen from a hydrogen atom and a methyl radical;
wherein said at least one zwitterionic polymer is soluble in water to a concentration of 1% by weight at a pH below 6 and at 20° C.; and
b) at least one non-amino, non-volatile, water-insoluble silicone having a viscosity of greater than 300 centistokes,
optionally leaving said cosmetic or dermatological composition on said wet keratin substance for a period of time; and
rinsing out said cosmetic or dermatological composition with water.

34. The process according to claim 33, wherein said keratin substance is hair.

35. A process for enhancing the conditioning effect of a non-amino, non-volatile, water-insoluble silicone in a rinse-out composition comprising said silicone, wherein said process comprises adding to said composition at least one zwitterionic polymer resulting from the copolymerization of at least one monomer of formula (I):

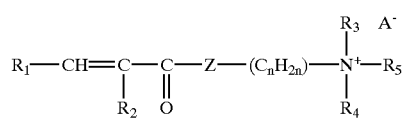

in which $R_1$ and $R_2$, which are identical or different, are chosen from a hydrogen atom and a methyl radical, and $R_3$, $R_4$ and $R_5$, which are identical or different, are chosen from linear and branched alkyl radicals containing from 1 to 4 carbon atoms,
Z is chosen from an NH group and an oxygen atom,
n is an integer from 2 to 5,
A⁻ is an anion of an organic or inorganic acid,
with at least one monomer of formula (II):

in which $R_6$ and $R_7$, which are identical or different, are chosen from a hydrogen atom and a methyl radical;
wherein said at least one zwitterionic polymer is soluble in water to a concentration of 1% by weight at a pH below 6 and at 20° C.;
wherein said composition, after said adding, further comprises a washing base present in an amount ranging from 4 to 30% by weight relative to the total weight of the composition, wherein the washing base comprises at least one surfactant.

36. The composition according to claim 1, wherein the composition is a shampoo.

37. A cosmetic or dermatological rinse-out composition, comprising, in a cosmetically or dermatologically acceptable aqueous medium,
a) at least one zwitterionic polymer resulting from the copolymerization of at least one monomer of formula (I):

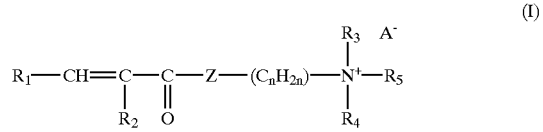

in which $R_1$ and $R_2$, which are identical or different, are chosen from a hydrogen atom and a methyl radical, and $R_3$, $R_4$ and $R_5$, which are identical or different, are chosen from linear and branched alkyl radicals containing from 1 to 4 carbon atoms,
Z is chosen from an NH group and an oxygen atom,
n is an integer from 2 to 5,
A⁻ is an anion of an organic or inorganic acid,
and at least one monomer of formula (II):

in which $R_6$ and $R_7$, which are identical or different, are chosen from a hydrogen atom and a methyl radical;
wherein said at least one zwitterionic polymer is soluble in water to a concentration of 1% by weight at a pH below 6 and at 20° C.; and
b) at least one non-amino, non-volatile, water-insoluble silicone having a viscosity of greater than 300 centistokes.

38. The composition according to claim 37, wherein said at least one non-amino, non-volatile, water-insoluble silicone has a viscosity of greater than 500 centistokes.

39. The composition according to claim 38, wherein said at least one non-amino, non-volatile, water-insoluble silicone has a viscosity of greater than 1000 centistokes.

40. The composition according to claim 37, wherein said at least one non-amino, non-volatile, water-insoluble silicone is chosen from:
(I) polyalkylsiloxanes;
(ii) polyarylsiloxanes;
(iii) polyalkylarylsiloxanes;
(iv) silicone gums;
(v) silicone resins;
(vi) polyorganosiloxanes containing one or more organofunctional groups directly attached to the siloxane chain or attached via a hydrocarbon-based radical;
(vii) block copolymers containing a polysiloxane-polyoxyalkylene linear block as a repeating unit;
(viii) grafted silicone polymers containing a non-silicone organic skeleton, comprising:
an organic main chain formed from organic monomers not containing silicone, and
at least one polysiloxane macromonomer which is grafted onto said organic main chain;
(ix) grafted silicone polymers containing a polysiloxane skeleton, comprising:
a polysiloxane main chain,
at least one organic macromonomer not containing silicon which is grafted onto said polysiloxane main chain;
(x) and mixtures thereof.

41. The composition according to claim 40, wherein for said grafted silicone polymers containing a non-silicone organic skeleton, at least one polysiloxane macromonomer is grafted to at least one end of said organic main chain, in addition to said at least one polysiloxane macromonomer grafted onto said organic main chain.

42. The composition according to claim 40, wherein for said grafted silicone polymers containing a polysiloxane skeleton, at least one organic macromonomer not containing silicon is grafted to at least one end of said polysiloxane main chain, in addition to said at least one organic macromonomer grafted onto said polysiloxane main chain.

43. The composition according to claim 40, wherein said polyalkylsiloxanes are chosen from:
linear polydimethylsiloxanes containing trimethylsilyl end groups, and
linear polydimethylsiloxanes containing hydroxydimethylsilyl end groups.

44. The composition according to claim 40, wherein said silicone gums are polydiorganopolysiloxanes having a number-average molecular mass ranging from 200,000 to 1,000,000.

45. The composition according to claim 40, wherein said silicone gums are chosen from:
polydimethylsiloxane,
poly((dimethylsiloxane)/(methylvinylsiloxane)),
poly((dimethylsiloxane)/(diphenylsiloxane)),
poly((dimethylsiloxane)/(phenylmethylsiloxane)),
poly((dimethylsiloxane)/(diphenylsiloxane)/(methylvinylsiloxane)).

46. The composition according to claim 40, wherein said silicone gums are chosen from:
a) mixtures formed from a polydimethylsiloxane hydroxylated at the end of the chain and a cyclic polydimethylsiloxane;
b) mixtures formed from a polydimethylsiloxane gum with a cyclic silicone; and
c) mixtures of a polydimethylsiloxane gum and a polydimethylsiloxane oil.

47. The composition according to claim 40, wherein said silicone resins are siloxane systems containing the units:
$R_2SiO_{2/2}$, $RSiO_{3/2}$, $SiO_{4/2}$, in which R is a hydrocarbon-based group containing from 1 to 6 carbon atoms or a phenyl group.

48. The composition according to claim 40, wherein said organomodified polyorganosiloxanes are chosen from those comprising:
a) polyethylenoxy groups, polypropylenoxy groups, and mixtures thereof;
b) (per)fluoro groups;
c) thiol groups;
d) carboxylate groups;
e) hydroxylated groups;
f) alkoxylated groups;
g) acyloxyalkyl groups;
h) amphoteric groups; and
i) bisulphite groups.

49. The composition according to claim 48, wherein said polyethylenoxy groups and polypropylenoxy groups further comprise alkyl groups.

50. The composition according to claim 40, wherein said block copolymers have the following formula:

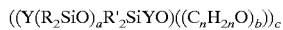

$((Y(R_2SiO)_aR'_2SiYO)((C_nH_{2n}O)_b))_c$ in which:
R and R', which are identical or different, are monovalent hydrocarbon-based radicals containing no aliphatic unsaturation,
n is an integer ranging from 2 to 4,
a is an integer greater than or equal to 5,
b is an integer greater than or equal to 4,
c is an integer greater than or equal to 4,
Y is a divalent organic group which is linked to the adjacent silicon atom via a carbon-silicon bond and to a polyoxyalkylene block via an oxygen atom,
each siloxane block, which comprises $(Y(R_2SiO)_aR'_2SiYO)$, has an average molecular weight ranging from 400 to 10,000, and each polyoxyalkylene block, which comprises $((C_nH_{2n}O)_b)$, has an average molecular weight ranging from 300 to 10,000,
said siloxane blocks are present in an amount ranging from 10% to 95% of the total weight of said block copolymer, and
said block copolymer has an average molecular weight of at least 3000.

51. The composition according to claim 37, wherein said at least one non-amino, non-volatile, water-insoluble silicone is present in an amount ranging from 0.001 to 20% by weight relative to the total weight of the composition.

52. The composition according to claim 51, wherein said at least one non-amino, non-volatile, water-insoluble silicone is present in an amount ranging from 0.01 to 10% by weight relative to the total weight of the composition.

53. The composition according to claim 37, wherein said at least one monomer of formula (I) is chosen from the following monomers:
dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylamino-propylacrylamide, wherein each of said monomers is quaternized.

54. The composition according to claim 53, wherein said monomers are quaternized with a $C_1$–$C_4$ alkyl halide or a $C_1$–$C_4$ dialkyl sulphate.

55. The composition according to claim 53, wherein said at least one monomer of formula (I) is chosen from acrylamidopropyltrimethylammonium chloride and methacrylamidopropyltrimethylammonium chloride.

56. The composition according to claim 37, wherein said at least one monomer of formula (II) is chosen from: acrylic acid, methacrylic acid, crotonic acid and 2-methyl-crotonic acid.

57. The composition according to claim 56, wherein said at least one monomer of formula (II) is acrylic acid.

58. The composition according to claim 37, wherein said at least one zwitterionic polymer is chosen from copolymers of acrylic acid and acrylamidopropyltrimethylammonium chloride, and copoylmers of acrylic acid and methacrylamidopropyltrimethylammonium chloride.

59. The composition according to claim 37, wherein said at least one zwitterionic polymer is present in a concentration ranging from 0.01 to 20% by weight relative to the total weight of the composition.

60. The composition according to claim 59, wherein said at least one zwitterionic polymer is present in a concentration ranging from 0.1 to 10% by weight relative to the total weight of the composition.

61. The composition according to claim 37, wherein said composition has a pH ranging from 3 to 11.

62. The composition according to claim 37, further comprising a washing base which comprises at least one surfactant chosen from anionic, cationic, nonionic, amphoteric, and zwitterionic surfactants.

63. The composition according to claim 62, wherein said washing base is present in an amount ranging from 4 to 30% by weight relative to the total weight of the composition.

64. The composition according to claim 37, wherein said cosmetically or dermatologically acceptable aqueous medium comprises water or a mixture of water and at least one lower alcohol.

65. The composition according to claim 37, further comprising at least one additive chosen from sequestering agents, softeners, foam modifiers, dyes, pearlescent agents, moisturizers, antidandruff agents, anti-seborrhoeic agents, suspending agents, ceramides, pseudoceramides, fatty acids containing linear $C_{16}$–$C_{40}$ chains, fatty acids containing branched $C_{16}$–$C_{40}$ chains, hydroxy acids, electrolytes, thickeners, fatty acid esters, fatty acid esters of glycerol, surfactants, fragrances, preserving agents, silicone sunscreens, non-silicone sunscreens, proteins, vitamins, ionic or nonionic polymers, water-soluble silicones, plant oils, animal oils, mineral oils, and synthetic oils.

66. The composition according to claim 37, wherein said composition is a rinse-out product for washing, conditioning, or styling hair, or for a combination of any two or three of washing, conditioning, and styling hair.

* * * * *